US005998450A

United States Patent [19]

Eicken et al.

[11] Patent Number: 5,998,450

[45] Date of Patent: Dec. 7, 1999

[54] HETEROCYCLICALLY SUBSTITUTED BIPHENYLAMINE DERIVATIVES, THEIR PREPARATION AND THEIR USE AS FUNGICIDES

[75] Inventors: Karl Eicken, Wachenheim; Harald Rang, Altrip; Albrecht Harreus, Ludwigshafen; Norbert Götz, Worms; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 09/011,717

[22] PCT Filed: Aug. 26, 1996

[86] PCT No.: PCT/EP96/03753

§ 371 Date: Feb. 17, 1998

§ 102(e) Date: Feb. 17, 1998

[87] PCT Pub. No.: WO97/08148

PCT Pub. Date: Mar. 6, 1997

[30] Foreign Application Priority Data

Aug. 30, 1995 [DE] Germany ........................... 195 31 813

[51] Int. Cl.[6] ......................... C07D 213/82; A61K 31/44

[52] U.S. Cl. .......................... 514/355; 514/365; 514/403; 546/316; 548/200; 548/374.1

[58] Field of Search ............................ 546/316; 548/200, 548/374.1; 514/355, 365, 403

[56] References Cited

U.S. PATENT DOCUMENTS

| | | | |
|---|---|---|---|
| 4,001,416 | 1/1977 | Pommer et al. | 424/266 |
| 4,214,090 | 7/1980 | Huppatz | 548/377 |
| 5,330,995 | 7/1994 | Eicken et al. | 514/355 |
| 5,438,070 | 8/1995 | Eicken et al. | 514/403 |
| 5,480,897 | 1/1996 | Eicken et al. | 514/365 |
| 5,556,988 | 9/1996 | Eicken et al. | 514/406 |
| 5,589,493 | 12/1996 | Eicken et al. | 546/316 |

FOREIGN PATENT DOCUMENTS

| | | |
|---|---|---|
| 545 099 | 6/1993 | European Pat. Off. . |
| 589 301 | 3/1994 | European Pat. Off. . |
| 95/25723 | 9/1995 | WIPO . |

OTHER PUBLICATIONS

Synthetic Connections to the Aromatic Directed . . . Sharp et al. 5093–5096.

Chem Abst. JP 07145156–A 1993.

Chem. Abst. vol. 123, 1994 p. 1246.

*Primary Examiner*—Jane Fan
*Attorney, Agent, or Firm*—Keil & Weinkauf

[57] ABSTRACT

Biphenylamides of the general formula I (I)

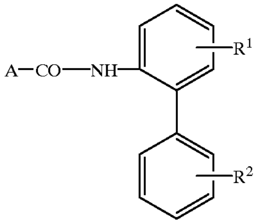

and their salts (A=

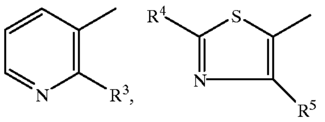

or

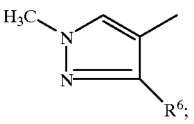

$R^1$=F; $R^2$=H, halogen, alkyl, $CF_3$, alkoxy, alkylthio; $R^3$=Cl, $CF_3$; $R^4$=H, $CH_3$; $R^5$=Cl, $CH_3$, $CHF_2$, $CF_3$; $R^6$=$CH_3$, $CHF_2$, $CF_3$), and compositions comprising I, the preparation of I and of the compositions, and of the use of both of them for controlling harmful fungi.

16 Claims, No Drawings

HETEROCYCLICALLY SUBSTITUTED BIPHENYLAMINE DERIVATIVES, THEIR PREPARATION AND THEIR USE AS FUNGICIDES

This case is filed under 371 PCT/EP96/03753 now WO 97/08,148.

The present invention relates to biphenylamides of the general formula I (I)

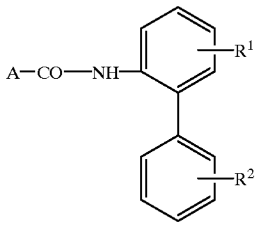

and to their salts where the radicals $R^1$, $R^2$ and A have the following meanings:

$R^1$ is fluorine;

$R^2$ is hydrogen, halogen, $C_1$–$C_4$-alkyl, trifluoromethyl, $C_1$–$C_4$-alkoxy or $C_1$–$C_4$-alkylthio;

A is (A1)

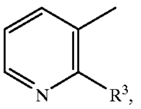

(A2)

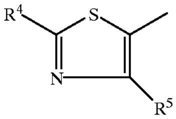

or (A3)

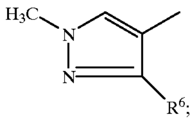

where the substituents $R^3$, $R^4$, $R^5$ and $R^6$, in turn, have the following meanings:

$R^3$ is chlorine or trifluoromethyl;

$R^4$ is hydrogen or methyl;

$R^5$ is chlorine, methyl, difluoromethyl or trifluoromethyl;

$R^6$ is methyl, difluoromethyl or trifluoromethyl.

Furthermore, the invention relates to a process for the preparation of the compounds I, to compositions comprising I, to a method of controlling harmful fungi, and to the use of the compounds I, of their salts or of the compositions for this purpose.

Fungicidal biphenylamides of the type I are disclosed in the following publications: DE-A 24 17 216, EP-A 545 099 and EP-A 589 301. However, the active ingredients mentioned in these publications are not yet satisfactory with a view to their activity.

It was therefore an object of the present invention to provide biphenylamides which have an improved activity against harmful fungi.

We have found that this object is achieved by the compounds I defined at the outset.

We have furthermore found compositions which comprise the compounds I or salts thereof and a process for the preparation of I and of the compositions. We have also found a method of controlling harmful fungi and the use of the compounds I, of their salts or of the compositions for this purpose.

The compounds I can be obtained in a manner known per se from the corresponding carboxylic acid halides II and the biphenylamines III with the aid of a base.

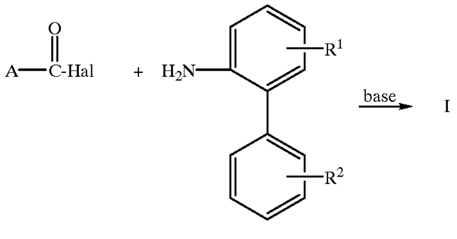

II III

Hal is halogen, preferably chlorine or bromine;

$R^1$ is fluorine;

$R^2$ is hydrogen, halogen, $C_1$–$C_4$-alkyl, trifluoromethyl, $C_1$–$C_4$-alkoxy or $C_1$–$C_4$-alkylthio;

(A1)

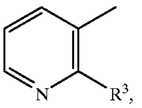

(A2)

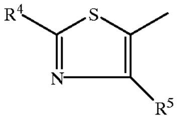

or (A3)

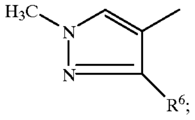

where the substituents $R^3$, $R^4$, $R^5$ and $R^6$, in turn, have the following meanings:

$R^3$ is chlorine or trifluoromethyl;

$R^4$ is hydrogen or methyl;

$R^5$ is chlorine, methyl, difluoromethyl or trifluoromethyl;

$R^6$ is methyl, difluoromethyl or trifluoromethyl.

As regards the reaction conditions for the preparation of the compounds I and the origin of the starting compounds II, compare, for example, EP-A 589 301 and EP-A 545 099.

Those biphenylamines III which are not generally known can be obtained in a manner known per se (compare, for example, Tetrahedron Letters 28, page 5093 to page 5096, 1987).

The invention also encompasses the salts of the acid-resistant compounds I which contain basic centers, especially basic nitrogen atoms, in particular with mineral acids, such as sulfuric acid and phosphoric acid or Lewis acids, such as zinc chloride. Normally, the type of salt is immaterial. Salts which are preferred for the purpose of the invention are those which do not damage the plants, areas, materials or spaces to be kept from harmful fungi and which do not adversely affect the activity of the compounds I. Such salts which are suitable for agricultural purposes are especially important.

The salts of the compounds I are accessible in a manner known per se, mainly by reacting the corresponding biphenylamides I with the abovementioned acids in water or an inert organic solvent at from −80 to 120° C., preferably 0 to 60° C.

In the definition of the compounds I given at the outset, collective terms are used which represent the following substituents:

Halogen: fluorine, chlorine, bromine and iodine;

Alkyl: straight-chain or branched alkyl groups having 1 to 8 carbon atoms, eg. $C_1$–$C_6$-alkyl, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkoxy: straight-chain or branched alkoxy groups having 1 to 4 carbon atoms, eg. $C_1$–$C_3$-alkoxy, such as methyloxy, ethyloxy, propyloxy and 1-methylethyloxy;

Alkylthio: straight-chain or branched alkyl groups having 1 to 4 carbon atoms (as mentioned above) which are bonded to the skeleton via a sulfur atom (—S—), eg. $C_1$–$C_4$-alkylthio, such as methylthio, ethylthio, propylthio, 1-methylethylthio, n-butylthio and tert-butylthio.

Preferred compounds I with a view to their biological activity against harmful fungi are those where $R^2$ is halogen, mainly fluorine, chlorine or bromine;

$C_1$–$C_4$-alkyl, mainly methyl, ethyl, propyl, 1-methylethyl, butyl, 1-methylpropyl, 2-methylpropyl or 1,1-dimethylethyl;

$C_1$–$C_4$-alkoxy, mainly methoxy, ethoxy, propoxy, 1-methylethoxy, butoxy, 1-methylpropoxy, 2-methylpropoxy or 1,1-dimethylethoxy;

alkylthio, mainly methylthio, ethylthio or propylthio.

Very especially preferred compounds I with a view to their use for controlling harmful fungi are those compiled in Tables 1 and 3 below.

TABLE 1

(I)

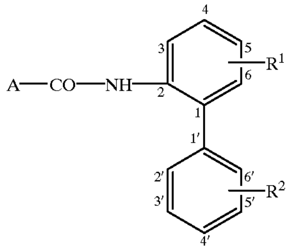

A1 = 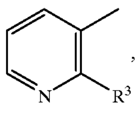 ,

TABLE 1-continued

A2 = 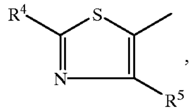 ,

A3 = 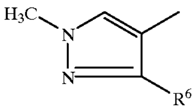

| No. | A | $R^1$ | $R^2$ | $R^3$ | $R^4$ | $R^5$ | $R^6$ |
|---|---|---|---|---|---|---|---|
| 1.1 | A1 | 4-F | H | Cl | — | — | — |
| 1.2 | A1 | 4-F | 2'-F | Cl | — | — | — |
| 1.3 | A1 | 4-F | 2'-$CH_3$ | Cl | — | — | — |
| 1.4 | A1 | 4-F | 2'-Cl | Cl | — | — | — |
| 1.5 | A1 | 4-F | 2'-$OCH_3$ | Cl | — | — | — |
| 1.6 | A1 | 4-F | 3'-F | Cl | — | — | — |
| 1.7 | A1 | 4-F | 3'-Cl | Cl | — | — | — |
| 1.8 | A1 | 4-F | 3'-$CH_3$ | Cl | — | — | — |
| 1.9 | A1 | 4-F | 3'-$OCH_3$ | Cl | — | — | — |
| 1.10 | A1 | 4-F | 3'-$OCH(CH_3)_2$ | Cl | — | — | — |
| 1.11 | A1 | 4-F | 3'-Br | Cl | — | — | — |
| 1.12 | A1 | 4-F | 4'-F | Cl | — | — | — |
| 1.13 | A1 | 4-F | 4'-Cl | Cl | — | — | — |
| 1.14 | A1 | 4-F | 4'-$CH_3$ | Cl | — | — | — |
| 1.15 | A1 | 4-F | 4'-$OCH_3$ | Cl | — | — | — |
| 1.16 | A1 | 4-F | 4'-$SCH_3$ | Cl | — | — | — |
| 1.17 | A1 | 4-F | 4'-$CF_3$ | Cl | — | — | — |
| 1.18 | A1 | 5-F | 2'-F | Cl | — | — | — |
| 1.19 | A1 | 5-F | 2'-$CH_3$ | Cl | — | — | — |
| 1.20 | A1 | 5-F | 2'-Cl | Cl | — | — | — |
| 1.21 | A1 | 5-F | 2'-$OCH_3$ | Cl | — | — | — |
| 1.22 | A1 | 5-F | 3'-F | Cl | — | — | — |
| 1.23 | A1 | 5-F | 3'-Cl | Cl | — | — | — |
| 1.24 | A1 | 5-F | 3'-$CH_3$ | Cl | — | — | — |
| 1.25 | A1 | 5-F | 3'-$OCH_3$ | Cl | — | — | — |
| 1.26 | A1 | 5-F | 3'-$OCH(CH_3)_2$ | Cl | — | — | — |
| 1.27 | A1 | 5-F | 3'-Br | Cl | — | — | — |
| 1.28 | A1 | 5-F | 4'-$OCH_3$ | Cl | — | — | — |
| 1.29 | A1 | 5-F | 4'-$SCH_3$ | Cl | — | — | — |
| 1.30 | A1 | 5-F | 4'-$CF_3$ | Cl | — | — | |
| 1.31 | A1 | 6-F | H | Cl | — | — | — |
| 1.32 | A1 | 6-F | 2'-F | Cl | — | — | — |
| 1.33 | A1 | 6-F | 2'-$CH_3$ | Cl | — | — | — |
| 1.34 | A1 | 6-F | 2'-Cl | Cl | — | — | — |
| 1.35 | A1 | 6-F | 2'-$OCH_3$ | Cl | — | — | — |
| 1.36 | A1 | 6-F | 3'-F | Cl | — | — | — |
| 1.37 | A1 | 6-F | 3'-Cl | Cl | — | — | — |
| 1.38 | A1 | 6-F | 3'-$CH_3$ | Cl | — | — | — |
| 1.39 | A1 | 6-F | 3'-$OCH_3$ | Cl | — | — | — |
| 1.40 | A1 | 6-F | 3'-$OCH(CH_3)_2$ | Cl | — | — | — |
| 1.41 | A1 | 6-F | 3'-Br | Cl | — | — | — |
| 1.42 | A1 | 6-F | 4'-$CH_3$ | Cl | — | — | — |
| 1.43 | A1 | 6-F | 4'-$OCH_3$ | Cl | — | — | — |
| 1.44 | A1 | 6-F | 4'-$SCH_3$ | Cl | — | — | — |
| 1.45 | A1 | 6-F | 4'-$CF_3$ | Cl | — | — | — |
| 1.46 | A1 | 3-F | H | Cl | — | — | — |
| 1.47 | A1 | 3-F | 2'-F | Cl | — | — | — |
| 1.48 | A1 | 3-F | 2'-$CH_3$ | Cl | — | — | — |
| 1.49 | A1 | 3-F | 2'-Cl | Cl | — | — | — |
| 1.50 | A1 | 3-F | 2'-$OCH_3$ | Cl | — | — | — |
| 1.51 | A1 | 3-F | 3'-F | Cl | — | — | — |
| 1.52 | A1 | 3-F | 3'-Cl | Cl | — | — | — |
| 1.53 | A1 | 3-F | 3'-$CH_3$ | Cl | — | — | — |
| 1.54 | A1 | 3-F | 3'-$OCH_3$ | Cl | — | — | — |
| 1.55 | A1 | 3-F | 3'-$OCH(CH_3)_2$ | Cl | — | — | — |
| 1.56 | A1 | 3-F | 3'-Br | Cl | — | — | — |
| 1.57 | A1 | 3-F | 4'-F | Cl | — | — | — |
| 1.58 | A1 | 3-F | 4'-Cl | Cl | — | — | — |
| 1.59 | A1 | 3-F | 4'-$CH_3$ | Cl | — | — | — |
| 1.60 | A1 | 3-F | 4'-$OCH_3$ | Cl | — | — | — |
| 1.61 | A1 | 3-F | 4'-$SCH_3$ | Cl | — | — | — |
| 1.62 | A1 | 3-F | 4'-$CF_3$ | Cl | — | — | — |
| 1.63 | A2 | 4-F | H | — | $CH_3$ | $CF_3$ | — |
| 1.64 | A2 | 4-F | 3'-F | — | $CH_3$ | $CF_3$ | — |

TABLE 1-continued

| | | | | | | | |
|---|---|---|---|---|---|---|---|
| 1.65 | A2 | 4-F | 3'-Cl | — | $CH_3$ | $CF_3$ | — |
| 1.66 | A2 | 4-F | 3'-$CH_3$ | — | $CH_3$ | $CF_3$ | — |
| 1.67 | A2 | 4-F | 3'-$OCH_3$ | — | $CH_3$ | $CF_3$ | — |
| 1.68 | A2 | 4-F | 3'-$OCH(CH_3)_2$ | — | $CH_3$ | $CF_3$ | — |
| 1.69 | A2 | 4-F | 3'-Br | — | $CH_3$ | $CF_3$ | — |
| 1.70 | A2 | 4-F | 4'-F | — | $CH_3$ | $CF_3$ | — |
| 1.71 | A2 | 4-F | 4'-Cl | — | $CH_3$ | $CF_3$ | — |
| 1.72 | A2 | 4-F | 4'-$CH_3$ | — | $CH_3$ | $CF_3$ | — |
| 1.73 | A2 | 4-F | 4'-$OCH_3$ | — | $CH_3$ | $CF_3$ | — |
| 1.74 | A2 | 4-F | 4'-$SCH_3$ | — | $CH_3$ | $CF_3$ | — |
| 1.75 | A2 | 4-F | 4'-$CF_3$ | — | $CH_3$ | $CF_3$ | — |
| 1.76 | A2 | 5-F | 3'-F | — | $CH_3$ | $CF_3$ | — |
| 1.77 | A2 | 5-F | 3'-Cl | — | $CH_3$ | $CF_3$ | — |
| 1.78 | A2 | 5-F | 3'-$CH_3$ | — | $CH_3$ | $CF_3$ | — |
| 1.79 | A2 | 5-F | 3'-$OCH_3$ | — | $CH_3$ | $CF_3$ | — |
| 1.80 | A2 | 5-F | 3'-$OCH(CH_3)_2$ | — | $CH_3$ | $CF_3$ | — |
| 1.81 | A2 | 5-F | 3'-Br | — | $CH_3$ | $CF_3$ | — |
| 1.82 | A2 | 5-F | 4'-$OCH_3$ | — | $CH_3$ | $CF_3$ | — |
| 1.83 | A2 | 5-F | 4'-$SCH_3$ | — | $CH_3$ | $CF_3$ | — |
| 1.84 | A2 | 5-F | 4'-$CF_3$ | — | $CH_3$ | $CF_3$ | — |
| 1.85 | A2 | 6-F | H | — | $CH_3$ | $CF_3$ | — |
| 1.86 | A2 | 6-F | 3'-F | — | $CH_3$ | $CF_3$ | — |
| 1.87 | A2 | 6-F | 3'-Cl | — | $CH_3$ | $CF_3$ | — |
| 1.88 | A2 | 6-F | 3'-$CH_3$ | — | $CH_3$ | $CF_3$ | — |
| 1.89 | A2 | 6-F | 3'-$OCH_3$ | — | $CH_3$ | $CF_3$ | — |
| 1.90 | A2 | 6-F | 3'-$OCH(CH_3)_2$ | — | $CH_3$ | $CF_3$ | — |
| 1.91 | A2 | 6-F | 3'-Br | — | $CH_3$ | $CF_3$ | — |
| 1.92 | A2 | 6-F | 4'-$CH_3$ | — | $CH_3$ | $CF_3$ | — |
| 1.93 | A2 | 6-F | 4'-$OCH_3$ | — | $CH_3$ | $CF_3$ | — |
| 1.94 | A2 | 6-F | 4'-$SCH_3$ | — | $CH_3$ | $CF_3$ | — |
| 1.95 | A2 | 6-F | 4'-$CF_3$ | — | $CH_3$ | $CF_3$ | — |
| 1.96 | A2 | 4-F | H | — | $CH_3$ | $CH_3$ | — |
| 1.97 | A2 | 4-F | 3'-F | — | $CH_3$ | $CH_3$ | — |
| 1.98 | A2 | 4-F | 3'-Cl | — | $CH_3$ | $CH_3$ | — |
| 1.99 | A2 | 4-F | 3'-$CH_3$ | — | $CH_3$ | $CH_3$ | — |
| 1.100 | A2 | 4-F | 3'-$OCH_3$ | — | $CH_3$ | $CH_3$ | — |
| 1.101 | A2 | 4-F | 3'-$OCH(CH_3)_2$ | — | $CH_3$ | $CH_3$ | — |
| 1.102 | A2 | 4-F | 3'-Br | — | $CH_3$ | $CH_3$ | — |
| 1.103 | A2 | 4-F | 4'-F | — | $CH_3$ | $CH_3$ | — |
| 1.104 | A2 | 4-F | 4'-Cl | — | $CH_3$ | $CH_3$ | — |
| 1.105 | A2 | 4-F | 4'-$CH_3$ | — | $CH_3$ | $CH_3$ | — |
| 1.106 | A2 | 4-F | 4'-$OCH_3$ | — | $CH_3$ | $CH_3$ | — |
| 1.107 | A2 | 4-F | 4'-$SCH_3$ | — | $CH_3$ | $CH_3$ | — |
| 1.108 | A2 | 4-F | 4'-$CF_3$ | — | $CH_3$ | $CH_3$ | — |
| 1.109 | A2 | 5-F | H | — | $CH_3$ | $CH_3$ | — |
| 1.110 | A2 | 5-F | 3'-F | — | $CH_3$ | $CH_3$ | — |
| 1.111 | A2 | 5-F | 3'-Cl | — | $CH_3$ | $CH_3$ | — |
| 1.112 | A2 | 5-F | 3'-$CH_3$ | — | $CH_3$ | $CH_3$ | — |
| 1.113 | A2 | 5-F | 3'-$OCH_3$ | — | $CH_3$ | $CH_3$ | — |
| 1.114 | A2 | 5-F | 3'-$OCH(CH_3)_2$ | — | $CH_3$ | $CH_3$ | — |
| 1.115 | A2 | 5-F | 3'-Br | — | $CH_3$ | $CH_3$ | — |
| 1.116 | A2 | 5-F | 4'-F | — | $CH_3$ | $CH_3$ | — |
| 1.117 | A2 | 5-F | 4'-Cl | — | $CH_3$ | $CH_3$ | — |
| 1.118 | A2 | 5-F | 4'-$CH_3$ | — | $CH_3$ | $CH_3$ | — |
| 1.119 | A2 | 5-F | 4'-$OCH_3$ | — | $CH_3$ | $CH_3$ | — |
| 1.120 | A2 | 5-F | 4'-$SCH_3$ | — | $CH_3$ | $CH_3$ | — |
| 1.121 | A2 | 5-F | 4'-$CF_3$ | — | $CH_3$ | $CH_3$ | — |
| 1.122 | A2 | 6-F | H | — | $CH_3$ | $CH_3$ | — |
| 1.123 | A2 | 6-F | 3'-F | — | $CH_3$ | $CH_3$ | — |
| 1.124 | A2 | 6-F | 3'-$CH_3$ | — | $CH_3$ | $CH_3$ | — |
| 1.125 | A2 | 6-F | 3'-Cl | — | $CH_3$ | $CH_3$ | — |
| 1.126 | A2 | 6-F | 3'-$OCH_3$ | — | $CH_3$ | $CH_3$ | — |
| 1.127 | A2 | 6-F | 3'-Br | — | $CH_3$ | $CH_3$ | — |
| 1.128 | A2 | 6-F | 3'-Cl | — | $CH_3$ | $CH_3$ | — |
| 1.129 | A2 | 6-F | 3'-$CH_3$ | — | $CH_3$ | $CH_3$ | — |
| 1.130 | A2 | 6-F | 3'-$OCH_3$ | — | $CH_3$ | $CH_3$ | — |
| 1.131 | A2 | 6-F | 3'-$OCH(CH_3)_2$ | — | $CH_3$ | $CH_3$ | — |
| 1.132 | A2 | 6-F | 3'-Br | — | $CH_3$ | $CH_3$ | — |
| 1.133 | A2 | 6-F | 4'-F | — | $CH_3$ | $CH_3$ | — |
| 1.134 | A2 | 6-F | 4'-Cl | — | $CH_3$ | $CH_3$ | — |
| 1.135 | A2 | 6-F | 4'-$CH_3$ | — | $CH_3$ | $CH_3$ | — |
| 1.136 | A2 | 6-F | 4'-$OCH_3$ | — | $CH_3$ | $CH_3$ | — |
| 1.137 | A2 | 6-F | 4'-$SCH_3$ | — | $CH_3$ | $CH_3$ | — |
| 1.138 | A2 | 6-F | 4'-$CF_3$ | — | $CH_3$ | $CH_3$ | — |
| 1.139 | A3 | 4-F | H | — | — | — | $CH_3$ |
| 1.140 | A3 | 4-F | 3'-$CH_3$ | — | — | — | $CH_3$ |
| 1.141 | A3 | 4-F | 3'-F | — | — | — | $CH_3$ |
| 1.142 | A3 | 4-F | 3'-Cl | — | — | — | $CH_3$ |
| 1.143 | A3 | 4-F | 3'-$CH_3$ | — | — | — | $CH_3$ |
| 1.144 | A3 | 4-F | 3'-$OCH_3$ | — | — | — | $CH_3$ |
| 1.145 | A3 | 4-F | 3'-$OCH(CH_3)_2$ | — | — | — | $CH_3$ |
| 1.146 | A3 | 4-F | 3'-Br | — | — | — | $CH_3$ |
| 1.147 | A3 | 4-F | 4'-F | — | — | — | $CH_3$ |
| 1.148 | A3 | 4-F | 4'-Cl | — | — | — | $CH_3$ |
| 1.149 | A3 | 4-F | 4'-$CH_3$ | — | — | — | $CH_3$ |
| 1.150 | A3 | 4-F | 4'-$OCH_3$ | — | — | — | $CH_3$ |
| 1.151 | A3 | 4-F | 4'-$SCH_3$ | — | — | — | $CH_3$ |
| 1.152 | A3 | 4-F | 4'-$CF_3$ | — | — | — | $CH_3$ |
| 1.153 | A3 | 5-F | H | — | — | — | $CH_3$ |
| 1.154 | A3 | 5-F | 3'-F | — | — | — | $CH_3$ |
| 1.155 | A3 | 5-F | 3'-Cl | — | — | — | $CH_3$ |
| 1.156 | A3 | 5-F | 3'-$CH_3$ | — | — | — | $CH_3$ |
| 1.157 | A3 | 5-F | 3'-$OCH_3$ | — | — | — | $CH_3$ |
| 1.158 | A3 | 5-F | 3'-$OCH(CH_3)_2$ | — | — | — | $CH_3$ |
| 1.159 | A3 | 5-F | 3'-Br | — | — | — | $CH_3$ |
| 1.160 | A3 | 5-F | 4'-$SCH_3$ | — | — | — | $CH_3$ |
| 1.161 | A3 | 5-F | 4'-$OCH_3$ | — | — | — | $CH_3$ |
| 1.162 | A3 | 5-F | 4'-$CF_3$ | — | — | — | $CH_3$ |
| 1.163 | A3 | 6-F | H | — | — | — | $CH_3$ |
| 1.164 | A3 | 6-F | 3'-F | — | — | — | $CH_3$ |
| 1.165 | A3 | 6-F | 3'-Cl | — | — | — | $CH_3$ |
| 1.166 | A3 | 6-F | 3'-$CH_3$ | — | — | — | $CH_3$ |
| 1.167 | A3 | 6-F | 3'-$OCH_3$ | — | — | — | $CH_3$ |
| 1.168 | A3 | 6-F | 3'-$OCH(CH_3)_2$ | — | — | — | $CH_3$ |
| 1.169 | A3 | 6-F | 3'-Br | — | — | — | $CH_3$ |
| 1.170 | A3 | 6-F | 4'-F | — | — | — | $CH_3$ |
| 1.171 | A3 | 6-F | 4'-Cl | — | — | — | $CH_3$ |
| 1.172 | A3 | 6-F | 4'-$CH_3$ | — | — | — | $CH_3$ |
| 1.173 | A3 | 6-F | 4'-$OCH_3$ | — | — | — | $CH_3$ |
| 1.174 | A3 | 6-F | 4'-$SCH_3$ | — | — | — | $CH_3$ |
| 1.175 | A3 | 6-F | 4'-$CF_3$ | — | — | — | $CH_3$ |
| 1.176 | A3 | 4-F | H | — | — | — | $CF_3$ |
| 1.177 | A3 | 4-F | 3'-F | — | — | — | $CF_3$ |
| 1.178 | A3 | 4-F | 3'-Cl | — | — | — | $CF_3$ |
| 1.179 | A3 | 4-F | 3'-$CH_3$ | — | — | — | $CF_3$ |
| 1.180 | A3 | 4-F | 3'-$OCH_3$ | — | — | — | $CF_3$ |
| 1.181 | A3 | 4-F | 3'-$OCH(CH_3)_2$ | — | — | — | $CF_3$ |
| 1.182 | A3 | 4-F | 3'-Br | — | — | — | $CF_3$ |
| 1.183 | A3 | 4-F | 4'-F | — | — | — | $CF_3$ |
| 1.184 | A3 | 4-F | 4'-Cl | — | — | — | $CF_3$ |
| 1.185 | A3 | 4-F | 4'-$CH_3$ | — | — | — | $CF_3$ |
| 1.186 | A3 | 4-F | 4'-$OCH_3$ | — | — | — | $CF_3$ |
| 1.187 | A3 | 4-F | 4'-$SCH_3$ | — | — | — | $CF_3$ |
| 1.188 | A3 | 4-F | 4'-$CF_3$ | — | — | — | $CF_3$ |
| 1.189 | A3 | 5-F | H | — | — | — | $CF_3$ |
| 1.190 | A3 | 5-F | 3'-F | — | — | — | $CF_3$ |
| 1.191 | A3 | 5-F | 3'-Cl | — | — | — | $CF_3$ |
| 1.192 | A3 | 5-F | 3'-$CH_3$ | — | — | — | $CF_3$ |
| 1.193 | A3 | 5-F | 3'-$OCH_3$ | — | — | — | $CF_3$ |
| 1.194 | A3 | 5-F | 3'-$OCH(CH_3)_2$ | — | — | — | $CF_3$ |
| 1.195 | A3 | 5-F | 3'-Br | — | — | — | $CF_3$ |
| 1.196 | A3 | 5-F | 4'-$OCH_3$ | — | — | — | $CF_3$ |
| 1.197 | A3 | 5-F | 4'-$SCH_3$ | — | — | — | $CF_3$ |
| 1.198 | A3 | 5-F | 4'-$CF_3$ | — | — | — | $CF_3$ |
| 1.199 | A3 | 6-F | H | — | — | — | $CF_3$ |
| 1.200 | A3 | 6-F | 3'-F | — | — | — | $CF_3$ |
| 1.201 | A3 | 6-F | 3'-Cl | — | — | — | $CF_3$ |
| 1.202 | A3 | 6-F | 3'-$CH_3$ | — | — | — | $CF_3$ |
| 1.203 | A3 | 6-F | 3'-$OCH_3$ | — | — | — | $CF_3$. |
| 1.204 | A3 | 6-F | 3'-$OCH(CH_3)_2$ | — | — | — | $CF_3$ |
| 1.205 | A3 | 6-F | 3'-Br | — | — | — | $CF_3$ |
| 1.206 | A3 | 6-F | 4'-$CH_3$ | — | — | — | $CF_3$ |
| 1.207 | A3 | 6-F | 4'-$OCH_3$ | — | — | — | $CF_3$ |
| 1.208 | A3 | 6-F | 4'-$SCH_3$ | — | — | — | $CF_3$ |
| 1.209 | A3 | 6-F | 4'-$CF_3$ | — | — | — | $CF_3$ |

The novel compounds of the formula I are suitable as fungicides.

The novel compounds I and their salts can be used, for example, in the form of directly sprayable solutions, powders, suspensions, also highly-concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

Normally, the plants are sprayed or dusted with the active ingredients or the seeds of the plants are treated with the active ingredients.

The formulations are prepared using customary formulation auxiliaries—as described below—and in a manner known per se, eg. by extending the active ingredient with solvents and/or carriers, if desired using emulsifiers and dispersants, it also being possible for other organic solvents to be used as auxiliary solvents if water is used as diluent. Suitable auxiliaries are essentially: solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide), and water; carriers, such as ground natural minerals (eg. kaolins, clays, talc, chalk) and ground synthetic minerals (eg. highly-disperse silica, silicates); emulsifiers, such as non-ionic and anionic emulsifiers (eg. polyoxyethylene fatty alcohol ethers, alkylsulfonates and arylsulfonates), and dispersants, such as lignin-sulfite waste liquors and methylcellulose.

Suitable surfactants are the alkali metal salts, alkaline earth metal salts and ammonium salts of aromatic sulfonic acids, eg. lignosulfonic acid, phenolsulfonic acid, naphthalenesulfonic acid and dibutylnaphthalenesulfonic acid, and of fatty acids, of alkylsulfonates and alkylarylsulfonates, of alkylsulfates, lauryl ether sulfates and fatty alcohol sulfates, and salts of sulfated hexa-, hepta- and octadecanols, and of fatty alcohol glycol ether; condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or non-ylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active ingredients with a solid carrier.

Granules, eg. coated granules, impregnated granules and homogeneous granules, can be prepared by binding the active ingredients to solid carriers. Solid carriers are mineral earths such as silica gel, silicas, silicates, talc, kaolin, limestone, lime, chalk, bole, loess, clay, dolomite, diatomaceous earth, calcium sulfate, magnesiumsulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powder, or other solid carriers.

Examples of such preparations are:

I. A solution of 90 parts by weight of a compound I according to the invention and 10 parts by weight of N-methyl-2-pyrrolidone which is suitable for use in the form of microdrops;

II. A mixture of 10 parts by weight of a compound I according to the invention, 70 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water.

III. An aqueous dispersion of 10 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. An aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mol of ethylene oxide to 1 mol of castor oil; A mixture, ground in a hammer mill, of 80 parts by weight of preferably a solid compound I according to the invention, 3 parts by weight of sodium diisobutylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. An intimate mixture of 3 parts by weight of a compound I according to the invention and 97 parts by weight of finely divided kaolin; this dust comprises 3% by weight of active ingredient;

VII. An intimate mixture of 30 parts by weight of a compound I according to the invention, 62 parts by weight of pulverulent silica gel, and 8 parts by weight of paraffin oil which had been sprayed onto the surface of this silica gel; this formulation imparts good adhesion properties to the active ingredient;

VIII. A stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. A stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds are distinguished by an outstanding activity against a broad spectrum of phytopathogenic fungi, in particular from the classes of the Deuteromycetes, Ascomycetes, Phycomycetes and Basidiomycetes. Some of them act systemically and can be employed as foliar- and soil-acting fungicides.

They are specially important for controlling a large number of fungi on a variety of crop plants such as wheat, rye, barley, oats, rice, maize, lawn, cotton, soya beans, coffee, sugarcane, grapevines, fruit species, ornamentals and vegetable species such as cucumbers, beans and cucurbits, and on the seeds of these plants.

The compounds are applied by treating the harmful fungi, their environment, or the plants, spaces, areas or materials to be kept free from them, with an effective amount of the active ingredients.

Application is effected before or after infection of the materials, plants or seeds by the fungi.

Specifically, the novel compounds are suitable for controlling the following plant diseases:

*Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton and lawns, Ustilago species on cereals and sugarcane, *Venturia inaequalis* (scab) on apples, Helminthosporium species on cereals, *Septoria nodorum* on wheat, *Botrytis cinerea* (gray mold) on strawberries, grapevines, ornamentals and vegetables, Monilinia species in fruit, *Cercospora arachidicola* on groundnuts, *Pseudocercosporella herpotrichoides* on wheat and barley, *Pyricularia oryzae* on rice, *Phytophthora infestans* on potatoes and tomatoes, Fusarium and Verticillium species on a variety of plants, *Plasmopara viticola* on grapevines, Alternaria species on vegetables and fruit.

The novel compounds. can also be employed in the protection of materials (protection of wood), eg. against *Paecilomyces variotii.*

In general, the fungicidal compositions comprise from 0.1 to 95, preferably from 0.5 to 90, % by weight of active ingredient.

Depending on the nature of the desired effect, the rates of application are from 0.025 to 2, preferably 0.1 to 1, kg of active ingredient per ha.

In the treatment of seed, amounts of from 0.001 to 50, preferably 0.01 to 10, g of active ingredient are generally required per kilogram of seed.

In the use form as fungicides, the compositions according to the invention can also be present together with other active ingredients, eg. with herbicides, insecticides, growth regulators, fungicides, or else with fertilizers.

A mixture with fungicides frequently results in a widened fungicidal spectrum of action.

The following list of fungicides together with which the compounds according to the invention can be applied is intended to illustrate the possible combinations, but not to impose any limitations:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethyl-thiophthalimide, N-dichlorofluoromethylthio-N', N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thione 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecyl-morpholine and its salts, 2,6-dimethyl-N-cyclododecylmorpholine and its salts, N-[3-(p-tert-butyl-phenyl)-2-methylpropyl]-cis-2,6-dimethylmorpholine, N-[3-(p-tert-butyl-phenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, α-(2-chlorophenyl)-α-(4-chlorophenyl)-5-pyrimidinemethanol, 5-butyl-2-dimethylamino-4-hydroxy-6-methylpyrimidine bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-yl-methyl]-1H-1,2,4-triazole, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenyl-acetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)-methylsilyl)methyl)-1H-1,2,4-triazole, strobilurins, such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoximino-[α-(2,5-dimethyloxy)-o-tolyl]acetamide.

Anilinopyrimidins, such as N-(4,6-dimethylpyrimidin-2-yl)aniline, N-([4-methyl-6-(1-propynyl))pyrimidin-2-yl] aniline, N-(4-methyl-6-cyclopropylpyrimidin-2-yl)aniline.

Phenylpyrroles, such as 4-(2,2-difluoro-1,3-benzodioxol-4-yl)-pyrrole-3-carbonitrile.

Cinnamamides, such as N-3-(4-chlorophenyl)-3-(3,4-dimethoxyphenyl)acryloylmorpholine.

SYNTHESIS EXAMPLES

The protocols for the preparation of the compounds I and III given in the synthesis examples which follow can be used for obtaining other compounds of the general formula I or III by changing the starting compounds. The physical data of the products thus prepared are also included in some cases in Tables 2 and 3 below.

Example 1

Precursor of the Type III

2-Amino-5,4'-difluorobiphenyl (No. 2.3 in Table 2)

2.4 g of tetrakis(triphenylphosphine)palladium, 15.1 g (0.108 mol) of 4-fluorophenylboronic acid and a solution of 30 g (0.282 mol) of sodium carbonate in 120 ml of water were added, under nitrogen, to a solution of 11.4 g (0.060 mol) of 2-bromo-4-fluoroaniline in 120 ml of 1,2-dimethoxyethane, and the mixture was refluxed for 8 hours. When cold, 200 ml of methyl tert-butyl ether and 100 ml of water were added. The organic phase was washed twice using in each case 120 ml of water, dried and concentrated. Chromatography of the residue on 50 g of silica gel using cyclohexane as the eluent gave 12.4 g of the title compound (m.p.: 67–69° C.).

TABLE 2

(III)

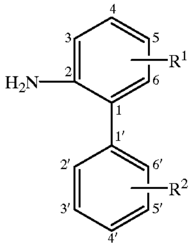

| No. | $R^1$ | $R^2$ | m.p. [° C.] |
|---|---|---|---|
| 2.1 | 5-F | H | oil |
| 2.2 | 5-F | 4'-Cl | 75–80 |
| 2.3 | 5-F | 4'-F | 67–9 |
| 2.4 | 5-F | 4'-$CH_3$ | 73–6 |
| 2.5 | 3-F | H | |
| 2.6 | 3-F | 4'-Cl | |
| 2.7 | 3-F | 4'-F | |
| 2.8 | 3-F | 4'-$CH_3$ | |
| 2.9 | 4-F | H | |
| 2.10* | 4-F | 4'-F | |
| 2.11 | 4-F | 4'-Cl | |
| 2.12 | 4-F | 4'-$CH_3$ | |
| 2.13 | 6-F | H | |
| 2.14 | 6-F | 4'-F | |
| 2.15 | 6-F | 4'-Cl | |
| 2.16 | 6-F | 4'-$CH_3$ | |

*Alternative synthesis: reduction of the corresponding nitro compound (cf. Chem. Ber. 64, page 1332 et seq., 1931; J. Chem. Soc., page 1159 et seq., 1930; Chem. Ber. 61, page 1407 et seq., 1928)

Example 2

Active Ingredient of the Type I

N-(4-Chloro-5-fluorobiphenyl-2-yl)-2-chloronicotinamide

A solution of 1.23 g (7 mmol) of 2-chloronicotinyl chloride in 3 ml of tetrahydrofuran was added dropwise at +5° C. to a solution of 1.55 g (7 mmol) of 2-amino-4'-chloro-5-fluorobiphenyl and 0.71 g (7 mmol) of triethylamine in 7 ml of tetrahydrofuran, and stirring was continued for 20 minutes at +5° C. and for 2 hours at room temperature. After the mixture had been stirred in 140 ml of water, the precipitate was filtered off with suction. Making the product into a paste using a mixture of diisopropyl ether and cyclohexane (1:2) gave 2.0 g of the title compound (m.p.: 131–136° C., No. 3.2 in Table 3).

TABLE 3

(I)

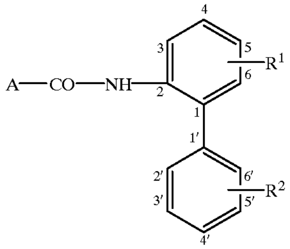

A1 = 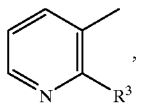 ,

A2 = 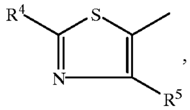 ,

A3 = 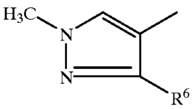

| No. | A | $R^1$ | $R^2$ | $R^3$ | $R^4$ | $R^5$ | $R^6$ | m.p. [° C.] |
|---|---|---|---|---|---|---|---|---|
| 3.1 | A1 | 5-F | 4'-F | Cl | — | — | — | 151–153 |
| 3.2 | A1 | 5-F | 4'-Cl | Cl | — | — | — | 131–136 |
| 3.3 | A1 | 5-F | 4'-$CH_3$ | Cl | — | — | — | 115–117 |
| 3.4 | A1 | 5-F | H | Cl | — | — | — | 131–134 |
| 3.5 | A2 | 5-F | 4'-F | — | $CH_3$ | $CF_3$ | — | 136–138 |
| 3.6 | A2 | 5-F | 4'-$CH_3$ | — | $CH_3$ | $CF_3$ | — | 106–108 |
| 3.7 | A2 | 5-F | 4'-Cl | — | $CH_3$ | $CF_3$ | — | 144–146 |
| 3.8 | A2 | 5-F | H | — | $CH_3$ | $CF_3$ | — | 146–148 |
| 3.9 | A3 | 5-F | 4'-F | — | — | — | $CF_3$ | 135–138 |
| 3.10 | A3 | 5-F | 4'-Cl | — | — | — | $CF_3$ | 136–140 |
| 3.11 | A3 | 5-F | 4'-$CH_3$ | — | — | — | $CF_3$ | 148–150 |
| 3.12 | A3 | 5-F | 4'-F | — | — | — | $CH_3$ | 163–166 |
| 3.13 | A3 | 5-F | 4'-Cl | — | — | — | $CH_3$ | 160–164 |
| 3.14 | A3 | 5-F | 4'-$CH_3$ | — | — | — | $CH_3$ | 154–157 |
| 3.15 | A1 | 6-F | 4'-F | Cl | — | — | — | 131–133 |
| 3.16 | A1 | 6-F | 4'-Cl | Cl | — | — | — | 150–152 |
| 3.17 | A2 | 6-F | 4'-F | — | $CH_3$ | $CF_3$ | — | 118–120 |
| 3.18 | A2 | 6-F | 4'-Cl | — | $CH_3$ | $CF_3$ | — | 123–124 |
| 3.19 | A3 | 6-F | 4'-F | — | — | — | $CF_3$ | 124–126 |
| 3.20 | A3 | 6-F | 4'-Cl | — | — | — | $CF_3$ | 127–128 |

Use Examples

In the following experiments on the fungicidal activity of the compounds I, an emulsion was used which was composed by 10% by weight of the active ingredient and 90% by weight of a mixture of 70% by weight of cyclohexanol, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols).

The desired concentrations of active ingredient were adjusted by diluting this emulsion with water.

Comparison compound "A" was 2'-ethyl-2-chloronicotinanilide, comparison compound "B" 2'-phenyl-2-chloronicotinanilide. Both compounds are disclosed in DE-A-24 17 216.

Use Example 1

*Botrytis cinerea*

Disks of green bell peppers were sprayed to drip point with an aqueous preparation prepared in accordance with the above protocol which comprised in each case 250 ppm of a single active ingredient. The following compounds according to the invention were used as active ingredients: 3.1, 3.2, 3.3, 3.4, 3.5, 3.6, 3.7, 3.9, 3.10, 3.11.

2 hours after the spray coating had dried on, the fruit disks were inoculated with a spore suspension of the fungus *Botrytis cinerea* which comprises $1.7\times10^6$ spores per ml of a 2% Biomalz solution. The fruit disks were subsequently incubated for 4 days at 18° C. in chambers with high atmospheric humidity.

Visual assessment showed a fungal disease level of 0–15% of the disk areas for the abovementioned compounds.

In the case of compound "A", the fungal disease level was 100% with otherwise identical experimental conditions.

Disks which had not been treated with a compound I or compound "A" showed a disease level of 100%.

Use Example 2

*Erysiphe graminis* var. *tritici*

Leaves of wheat seedlings grown in pots (cultivar "Fr ühgold") were sprayed with an aqueous preparation prepared in accordance with the above protocol which comprised in each case 250 ppm of a single active ingredient. The following compounds according to the invention were used as active ingredients: 3.2, 3.3, 3.5, 3.6, 3.7, 3.8, 3.9, 3.10, 3.11.

24 hours after the spraycoating had dried on, the leaves were dusted with oidia (spores) of powdery mildew of wheat (*Erysiphe graminis* var. *tritici*). The plants were subsequently incubated for 7 days at 20–22° C. and a relative atmospheric humidity of 75–80%.

Visual assessment showed a fungal disease level of 5–25% of the leaf area for the abovementioned compounds.

In the case of compound "A", the fungal disease level was 60% with otherwise identical experimental conditions. For "B", a disease level of 80% was determined.

Leaves which had not been treated with a compound I, "A" or "B" showed a disease level of 80%.

We claim:

1. A biphenylamide of the formula I (I)

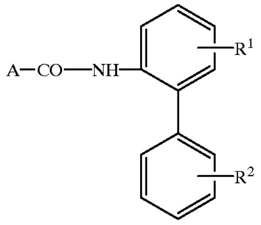

or a salt thereof where the radicals $R^1$, $R^2$ and A have the following meanings:

$R^1$ is fluorine;

$R^2$ is hydrogen, halogen, $C_1$–$C_4$-alkyl, trifluoromethyl, $C_1$–$C_4$-alkoxy or $C_1$–$C_4$-alkylthio;

A is a radical selected from the group consisting of

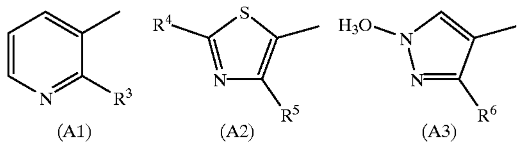

(A1) (A2) (A3)

where the substituents $R^3$, $R^4$, $R^5$ and $R^6$, in turn, have the following meanings:

$R^3$ is chlorine or trifluoromethyl;

$R^4$ is hydrogen or methyl;

$R^5$ is chlorine, methyl, difluoromethyl or trifluoromethyl; and $R^6$ is methyl, difluoromethyl or trifluoromethyl.

2. The biphenylamide of the formula I as defined in claim 1, wherein the radical $R^1$ is bonded to the 5- or the 6-position of the biphenyl radical.

3. The biphenylamide of the formula I as defined in claim 1, wherein $R^2$ is halogen.

4. The biphenylamide of the formula I as defined in claim 1, wherein $R^2$ is $C_1$–$C_4$-alkyl.

5. The biphenylamide of the formula I as defined in claim 1, wherein the radical $R^2$ is bonded to the 4'-position of the biphenyl radical.

6. The biphenylamide of the formula I as defined in claim 1, wherein A is (A1).

7. The biphenylamide of the formula I as defined in claim 6, wherein $R^3$ is chlorine.

8. The biphenylamide of the formula I as defined in claim 1, wherein A is (A2).

9. The biphenylamide of the formula I as defined in claim 8, wherein $R^4$ is methyl.

10. The biphenylamide of the formula I as defined in claim 8, wherein $R^5$ is trifluoromethyl.

11. The biphenylamide of the formula I as defined in claim 9, wherein $R^5$ is trifluoromethyl.

12. The biphenylamide of the formula I as defined in claim 1, wherein A is (A3).

13. The biphenylamide of the formula I as defined in claim 12, wherein $R^6$ is methyl.

14. The biphenylamide of the formula I as defined in claim 12, wherein $R^6$ is trifluoromethyl.

15. A composition which is suitable for controlling harmful fungi, comprising an effective amount of at least one compound of the formula I or of a salt thereof as defined in claim 1 and at least one customary formulation auxiliary.

16. A method of controlling harmful fungi, which comprises treating the plants to be kept free from said fungi, with an effective amount of at least one compound of the formula I or of a salt thereof as defined in claim 1.

* * * * *

UNITED STATES PATENT AND TRADEMARK OFFICE

CERTIFICATE OF CORRECTION

PATENT NO.: 5,998,450

DATED: December 7, 1999

INVENTOR(S): EICKEN et al.

It is certified that error appears in the above-identified patent and that said Letters Patent is hereby corrected as shown below:

On the title page: Item [54] and Col. 1, line 3,

"BIPHENYLAMINE" should be --BIPHENYLAMIDE--.

Col. 14, claim 1, line 10, in formula (A3), "$H_3O$" should be --$H_3C$--.

Signed and Sealed this

Eighteenth Day of July, 2000

Attest:

Q. TODD DICKINSON

*Attesting Officer*

*Director of Patents and Trademarks*